(12) United States Patent
Gagnon

(10) Patent No.: US 9,988,419 B2
(45) Date of Patent: Jun. 5, 2018

(54) PROTEIN PURIFICATION METHODS

(71) Applicant: AGENCY FOR SCIENCE, TECHNOLOGY AND RESEARCH, Connexis (SG)

(72) Inventor: Peter Stanley Gagnon, Centros (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 264 days.

(21) Appl. No.: 14/766,131

(22) PCT Filed: Feb. 5, 2014

(86) PCT No.: PCT/SG2014/000047
§ 371 (c)(1),
(2) Date: Aug. 5, 2015

(87) PCT Pub. No.: WO2014/123485
PCT Pub. Date: Aug. 14, 2014

(65) Prior Publication Data
US 2015/0376231 A1 Dec. 31, 2015

Related U.S. Application Data

(60) Provisional application No. 61/761,646, filed on Feb. 6, 2013, provisional application No. 61/764,966, filed on Feb. 14, 2013, provisional application No. 61/831,099, filed on Jun. 4, 2013, provisional application No. 61/859,772, filed on Jul. 29, 2013, provisional application No. 61/907,877, filed on Nov. 22, 2013.

(51) Int. Cl.
| C07K 1/30 | (2006.01) |
| C07K 16/00 | (2006.01) |
| B01D 15/36 | (2006.01) |
| C07K 16/28 | (2006.01) |

(52) U.S. Cl.
CPC .............. *C07K 1/303* (2013.01); *B01D 15/36* (2013.01); *C07K 1/30* (2013.01); *C07K 16/00* (2013.01); *C07K 16/2863* (2013.01)

(58) Field of Classification Search
None
See application file for complete search history.

(56) References Cited

U.S. PATENT DOCUMENTS

| 4,379,086 A | 4/1983 | Kimura et al. |
| 4,515,776 A | 5/1985 | Taniguchi et al. |
| 2008/0214795 A1 | 9/2008 | Ramanan et al. |
| 2010/0204455 A1 | 8/2010 | Gervais et al. |
| 2016/0272675 A1* | 9/2016 | Jungbauer .............. C07K 16/00 |

FOREIGN PATENT DOCUMENTS

| WO | WO 91/18009 | 11/1991 | | |
| WO | WO 2005/073252 | 8/2005 | | |
| WO | WO-2005073252 A1 * | 8/2005 | ............ | A61L 2/0011 |
| WO | WO-2010151632 A1 * | 12/2010 | ............... | C07K 1/30 |
| WO | WO 2012/169970 | 12/2012 | | |
| WO | WO-2012169970 A1 * | 12/2012 | ........... | B01D 15/166 |

OTHER PUBLICATIONS

Pete Gagnon "Purification tools for monoclonal antibodies" Validated Biosystems, Inc., pp. 1-254, 1996.*
Atha et al, "Mechanism of precipitation of proteins by polyethylene glycols", Journal of Biological Chemistry, vol. 256, No. 23, 1981, pp. 12108-12117.
Supplemental European Search report dated Sep. 2, 2016 for Appln. No. 14749299.5.
Extended European Search report dated Aug. 17, 2016 for Appln. No. 14749299.5.
Gagnon et al., "High productivity purification of immunoglobulin G monoclonal antibodies on starch-coated magnetic nanoparticles by steric exclusion of polyethylene glycol", Journal of Chromatography A, 1324, (2014), pp. 171-180.
Gan et al., "Characterization and removal of aggregates formed by nonspecific interaction of IgM monoclonal antibodies with chromatin catabolites during cell culture production", Journal of Chromatography A 1291, (2013), pp. 33-40.
International Search Report dated Apr. 14, 2014 for Appln. No. PCT/SG2014/000047.
Lain et al., "PEG precipitation: a powerful tool for monoclonal antibody purification", BioPharm, 2010, pp. 1-8.
Kuczewski et al., "A single-use purification process for the production of a monoclonal antibody produced in a PER.C6 human cell line", Biotechnology Journal, 2011, 6, pp. 56-65.
Nian et al, "Void exclusion of antibodies by grafted-ligand porous particle anion exchangers", Journal of Chromatography A, 1282, (2013), pp. 127-132.

(Continued)

*Primary Examiner* — Daniel E Kolker
*Assistant Examiner* — James L Rogers
(74) *Attorney, Agent, or Firm* — Pillsbury Winthrop Shaw Pittman LLP

(57) ABSTRACT

A method for the purification of a desired protein from a protein preparation includes conditioning the protein preparation by treatment with soluble organic multivalent ions, immobilized organic multivalent ions, or both, optionally in the presence of supersaturated allantoin, thereby removing at least 90% of chromatin, then (1) precipitating the desired protein with a nonionic organic polymer in the presence of non-protein-precipitating salts at greater than physiological concentration to provide a precipitate of the desired protein; or (2) precipitating the desired protein with a nonionic organic polymer in the absence of non-precipitating salts at greater than physiological concentration to provide a precipitate and subsequently washing the precipitate with a nonionic organic polymer in the presence of non-protein-precipitating salts at greater than physiological concentration.

10 Claims, No Drawings

(56) References Cited

OTHER PUBLICATIONS

Raweerith et al, "Fractionation of equine antivenom using caprylic acid precipitation in combination with cationic ion-exchange chromatography", Journal of Immunological Methods 282, (2003), pp. 63-72.
Singapore Written Opinion dated Nov. 29, 2016 for Appln. No. 11201505198W.
Gagnon, "Purification Tools for Monoclonal Antibodies", Validated Biosystems, 1996, pp. 1-269.

* cited by examiner

PROTEIN PURIFICATION METHODS

STATEMENT OF RELATED APPLICATION

This application claims priority to U.S. Provisional Application Nos. 61/761,646, filed Feb. 6, 2013, 61/764,966, filed Feb. 14, 2013, 61/831,099, filed Jun. 4, 2013, 61/859,772, filed Jul. 29, 2013, and 61/907,877, filed Nov. 22, 2013, each of which is incorporated herein by reference in its entirety.

BACKGROUND

Purification of recombinant proteins commonly begins with a clarification step in which cells and debris are removed so that the remaining supernatant can be processed by methods that would be hampered or rendered ineffective by the presence of cells and debris. Their removal commonly involves physical methods such as centrifugation and microfiltration. It sometimes involves the use of membrane or depth filters with anion exchange capabilities, or the addition of anion exchange polymers or particles directly to the antibody-containing harvest (Gagnon, P., *Purification Tools for Monoclonal Antibodies, Validated Biosystems*, Tucson, 1996; Kuczewski, M, et al, *Biopharm Int.* 23 (3) (2010) 20-25; Kuczewski, M., et al, *Biotechnol. J.,* 6 (2011) 56-65). Gan et al (J. Chromatography A-191 (2013) 33-40) have recently indicated that targeted removal of chromatin catabolites with soluble and insoluble forms of multivalent organic ions supports especially effective conditioning of cell culture harvests. Physical clarification methods typically achieve no significant chromatin reduction. Adding anion exchange particles to the harvest typically removes about half of the DNA. Some of the methods described by Gan et al (supra) remove 99% of chromatin, and may accurately be referred to as chromatin-directed clarification methods.

Purification of proteins by precipitation with polyethylene glycol (PEG) has been described. It is typically performed as an aqueous phase technique, where PEG is dissolved in an aqueous protein preparation and causes the protein to precipitate from that solution. The size and concentration of PEG are known process variables, as is pH (Gagnon 1996 supra; D. Atha, K., et al, *J. Biol. Chem.,* 256 (1981) 12108-12117; U.S. Patent Application Publication No. 2008/0214795, each of which are incorporated herein by reference. The closer the operating pH to the isoelectric point of the antibody, the lower the concentration of PEG required to achieve precipitation. It has been indicated that the concentration of non-protein-precipitating salts such as sodium chloride (NaCl) has little significant effect on selectivity (Atha et al supra), but the technique has been carried out in the presence of NaCl at concentrations up to about 0.1.7 M (10%, Gervais et al., U.S. Patent Application Publication No. 2010/0204455). It has also been demonstrated that PEG-mediated steric exclusion chromatography achieves higher IgG recovery and lower contaminant levels when PEG is combined with elevated concentrations of NaCl, and further noted that it largely suspends the influence of pH (P. Gagnon et al, J. Chromatogr. A 1324 (2014) 171-180). Combining PEG with the protein-precipitating salt sodium phosphate has been described (Gervais, supra; U.S. Pat. Nos. 4,379,086 and 4,515,776).

Removal of residual PEG after the precipitate is re-solubilized is a major challenge for the technique. Kuczewski et al supra removed it by performing cation exchange chromatography under conditions where IgG bound to the cation exchange column while the PEG flowed through. PEG removal is otherwise complicated by the fact that it occupies the same range of sizes, measured as hydrodynamic radius or diameter, as the proteins it is used to precipitate. This disqualifies the standard methods of size exclusion chromatography, dialysis, and diafiltration for PEG removal. Anion exchange chromatography in flow-through mode, as widely practiced with IgG monoclonal antibodies, is also unsuitable because the PEG flows through with the antibody.

SUMMARY

In some aspects, embodiments disclosed herein relate to methods for the purification of a desired protein from a protein preparation comprising conditioning the protein preparation by treatment with soluble organic multivalent ions, immobilized organic multivalent ions, or both, optionally in the presence of supersaturated allantoin, thereby removing at least 90% of chromatin, then (1) precipitating the desired protein with a non-ionic organic polymer in the presence of non-protein-precipitating salts at greater than physiological concentration to provide a precipitate of the desired protein, or (2) precipitating the desired protein with a nonionic organic polymer in the absence of non-precipitating salts at greater than physiological concentration to provide a precipitate and subsequently washing the precipitate with a nonionic organic polymer in the presence of non-protein-precipitating salts at greater than physiological concentration, wherein the precipitating or washing step is optionally carried out in the substantial absence of a protein-precipitating salt, and optionally without adjusting the pH of the desired protein to a value within 0.5 pH units of the isoelectric point of the desired protein, and optionally washing the precipitate with a protein-precipitating salt in the absence of a non-ionic organic polymer, where in the precipitating salt is present at a sufficient concentration to keep the desired protein in a precipitated state.

DETAILED DESCRIPTION

It has been discovered that conditioning of an antibody-containing protein preparation by exposure to soluble organic multivalent ions and/or organic multivalent ions immobilized on a solid surface under conditions where 90% or more of chromatin and chromatin catabolites are removed but the antibody remains soluble, enhances the ability of fractionation by PEG precipitation to an unexpectedly high degree. By way of illustration, where the conditioning step reduces contamination from host proteins by a factor of 30-70%, it surprisingly increases the ability of a subsequent PEG precipitation step to further reduce host protein contamination by 400-500% or more, particularly if the precipitating formula also contains an excess of non precipitating salts. This highlights the important point that chromatin-directed clarification methods do not aid subsequent purification merely by reducing the gross contaminant load, but by removing contaminants that interfere with a subsequent purification step. It has also been observed that the presence during precipitation of salts at concentrations greater than normal physiological levels dramatically reduces, and in some cases virtually nullifies, the need to adjust operating pH to, or close to, the isoelectric point of the desired protein. Washing the precipitated desired protein with a final wash comprising a protein-precipitating salt at a concentration adequate to keep the protein precipitated, but lacking PEG, provides the further benefit of removing PEG prior to resolubilizing the desired protein. Various combinations of these features remarkably enable combinations of a conditioning step and a precipitating step to reduce host cell contamination below levels achieved by high-functioning methods such as bioaffinity chromatography. In turn, this permits the disclosed methods to achieve a level of purification sufficient to support in vivo use of the purified desired protein with only a single additional fractionation step after resolubilizing the antibody. Experimental data demonstrate that the integrated method is broadly applicable to IgG and IgM antibodies. Its ability to effectively purify IgM antibodies indicates its applicability to purification of non-antibody proteins. Aspects of the methods disclosed herein are used in connection with methods disclosed in International Patent Application Nos. WO 2013180650, WO 2013180649, and WO 2013180655, each of which is incorporated herein by reference in its entirety.

In one or more embodiments, conditioning the protein preparation with organic multivalent ions comprises contacting the sample with an electropositive organic additive. In some such embodiments, the electropositive organic additive comprises at least one selected from the group consisting of ethacridine, methylene blue, cetyltrimethylammonium bromide. In some such embodiments, the concentration of such a species, or aggregate concentration of a combination of species is in the range of 0.001 to 1%, or 0.01 to 0.1%, or 0.02 to 0.05%. In some such embodiments the pH of the preparation may be adjusted up to an alkaline value that does not cause significant reduction of recovery of the desired protein. In one such embodiment where the desired protein is an IgG monoclonal antibody, the pH may be adjusted up to a pH value a half pH unit below the antibody isoelectric point, or higher if experimental results indicate that antibody recovery is acceptable, but such adjustments are not necessary. To the extent that any pH adjustment is made in the presence of elevated salt concentrations, a pH value within about 0.5 to about 1.0 pH units of the protein isoelectric point will suffice, or within about 1.5 pH units, or within about 2.0 pH units.

In one or more of the preceding embodiments, conditioning the protein preparation with organic multivalent ions comprises contacting the sample with an electronegative organic additive. In some such embodiments, the electronegative organic additive comprises at least one selected from the group consisting of heptanoic acid, octanoic acid, octenoic acid, nonanoic acid, nonenoic acid, decanoic acid, methyl blue. In some such embodiments, the concentration of such a species, or total concentration of a combination of species is in the range of 0.001 to 10%, or 0.01 to 1%, or 0.1 to 0.5%. In some such embodiments the pH of the preparation may be adjusted down to an acidic value that does not cause significant reduction of recovery of the desired protein. In some such embodiments, the pH of the preparation may be adjusted to the range of 3.5 to 6.5, 4.0 to 6.0, 4.5 to 5.5, 5.0 to 5.3, 5.15 to 5.25, or 5.2, or another intermediate value.

In one or more of the preceding embodiments, electropositive multivalent organic ions and electronegative multivalent organic ions may be employed to condition a preparation. In some such embodiments, an electropositive multivalent organic ion is contacted with the preparation in advance of the electronegative multivalent organic ion. In some such embodiments the electropositive multivalent organic ion is cetyltrimethylammonium at a concentration of about 0.01% and the electronegative multivalent organic multivalent ion is nonanoic acid at a concentration of about 0.4%. In some such embodiments, about 1% to about 2% allantoin may be present at any stage of the conditioning. In some such embodiments, the aggregate content of the conditioned preparation is lower by a factor of about 3 to 4 than in preparations where the electronegative multivalent organic ion is added first.

In one or more of the preceding embodiments, conditioning the protein preparation with organic multivalent ions comprises contacting the sample with undissolved allantoin. In some such embodiments, the added allantoin resident in a protein preparation may amount to about 0.6% to 50%, or 0.7 to 20%, or 0.8 to 10%, or 0.9 to 5%, or 1 to 2%, or an intermediate value.

In one or more of the preceding embodiments, conditioning the protein preparation with organic multivalent ions comprises contacting the sample with a nonionic or zwitterionic surfactant at a concentration lower than its critical micelle concentration.

In one or more of the preceding embodiments, conditioning of the protein preparation with organic multivalent ions comprises (i) providing a first component which is a first solid substrate having an electronegative surface; (ii) contacting the protein preparation with the first component, wherein the operating conditions substantially prevent the binding of the desired protein to the first component; and (iii) separating the desired protein with a reduced chromatin content from the first component. In some such embodiments, the first electronegative surface may be accompanied by a second electronegative surface.

In one or more of the preceding embodiments, conditioning of the protein preparation with organic multivalent ions comprises (i) providing a first component which is a first solid substrate having an electropositive surface; (ii) contacting the protein preparation with the first component, wherein the operating conditions substantially prevent the binding of the desired protein to the first component; and (iii) separating the desired protein with a reduced chromatin content from the first component. In some such embodiments, the first electropositive surface bears residues of 2(aminoethyl)amine. In some such embodiments, the first electropositive surface may be accompanied by a second electropositive surface.

In one or more of the preceding embodiments, conditioning of the protein preparation with organic multivalent ions comprises (i) providing a first component which is a first solid substrate having an electropositive surface; (ii) providing a second component which is a second solid substrate having an electronegative surface; (iii) contacting the protein preparation with the first and second components, wherein the first and second components are configured such that the protein preparation may contact both components simultaneously, wherein the operating conditions substantially prevent the binding of the desired protein to the first or second components; and (iv) separating the desired protein with a reduced chromatin content from the first and second components. In some such embodiments, the first electropositive surface bears residues of 2(aminoethyl)amine.

In one or more of the preceding embodiments, conditioning of the protein preparation with organic multivalent ions comprises (i) contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (ii) separating the protein preparation from the at least one surface-bound ligand.

In one or more of the preceding embodiments, a protein preparation already treated with a soluble electropositive or electronegative organic additive and/or a solid surface bearing an electronegative, electropositive, or metal affinity ligand, may be subsequently flowed through a device, the fluid-contact surface of which comprises positive charges.

In one embodiment illustrating application of a chromatin-directed clarification method, allantoin is added to a cell culture harvest in an amount of 1% (v/v). The cell culture may contain cells, or the cells may previously have been removed. Methylene blue is added to a concentration of 0.025% (w/v). Alternatively, ethacridine may be added to a concentration of 0.025%. Alternatively, 0.025% cetyltrimethylammonium bromide may be added to a concentration of 0.025%. Alternatively, a combination of these or other electropositive organic additives may be used at an combined concentration of 0.025%. The mixture is then incubated stirring for 2 hours. Particles bearing the electropositive metal affinity ligand 2(aminoethyl)amine (TREN) are added in an amount of 2-5% v:v. The mixture is incubated stirring for 4 hours then the solids are removed by any expedient means. The remaining solution containing the desired protein may be optionally flowed through a depth filter bearing positive charges on its fluid contact surface.

In another embodiment illustrating application of a chromatin-directed clarification method, allantoin is added to a cell culture harvest in an amount of 1% (v/v). The cell culture may contain cells, or the cells may previously have been removed. 0.6% heptanoic acid is added. Alternatively 0.4% octanoic acid is added. Alternatively 0.3% pelargonic acid is added. Alternatively 0.2% capric acid is added. Alternatively, 0.5% methyl blue is added. Alternatively, a combination of these or other electronegative organic additives may be used. The mixture is then incubated stirring for 2 hours. Particles bearing the electropositive metal affinity ligand 2(aminoethyl)amine (TREN) are added in an amount of 2-5% v:v. The mixture is incubated mixing for 4 hours then the solids removed by any expedient method. The remaining solution containing the desired protein may be optionally flowed through a depth filter bearing positive charges on its fluid contact surface.

In one or more of the previous embodiments, salt may be added to a clarification mixture to prevent loss of the desired protein through excessive interactions with a soluble or insoluble multivalent organic ion. In some such embodiments, NaCl may be added to increase conductivity to a level corresponding to about 200 mM, with a rough conductivity equivalent of about 20 mS/cm, for the purpose of preventing an IgM antibody or non-antibody protein from binding to components of a chromatin-directed clarification system. In other such embodiments, the NaCl concentration may be elevated to a greater or lesser degree to accommodate a particular recombinant protein. Appropriate salt concentrations for accommodating any particular protein can be quickly and easily estimated by applying a sample of the desired protein to a cation exchanger or an anion exchanger, eluting them with an increasing salt gradient, determining the conductivity at the center of the desired protein peak, then using that conductivity value for the clarification process.

In one or more of the preceding embodiments, the nonionic organic polymer used to precipitate the desired protein comprises polyethylene glycol.

In one or more of the previous embodiments, the PEG may be of an average size of 8 kDa, or 6 kDa, or 4 kDa, or 3 kDa, or 2 kDa, or an intermediate size. It will be understood by the person of skill in the art that the smaller the PEG, the higher the concentration required to achieve the same effect as a larger polymer.

In one or more of the previous embodiments, the nonionic organic polymer used to mediate precipitation may be a species other than PEG, for example polypropylene glycol, polyvinylpyrrolidone, dextran, cellulose, or other polymers.

In one or more of the preceding embodiments, the non-protein-precipitating salt combined with the nonionic organic polymer is sodium chloride with a conductivity in a range selected from the group consisting of (i) about 50 mS/cm to about 100 mS/cm; (ii) about 16 mS/cm to about 200 mS/cm, (iii) a conductivity greater than 160 mS/cm. For aqueous solutions of NaCl, 16 mS/cm corresponds to a NaCl concentration of about 160 mM, 50 mS/cm corresponds roughly to 600 mM, 160 mS/cm corresponds roughly to a concentration of about 2 M NaCl, and 200 mS/cm corresponds roughly to about 2.5 M NaCl. The disclosed methods may be practiced at NaCl concentration up to saturation, which occurs at slightly higher than 5 M, while a beneficial working range may generally be from about 0.5 to 1.5 M. Accurate conductivity measurements will be confounded by the presence of nonionic organic polymers, which depress apparent conductivity values with increasing polymer concentration and polymer size. Accurate conductivity measurements may be further confounded by poor linearity of some conductivity-monitoring devices. Accordingly, to the extent that conductivity is used as an index of salt concentration, the suggested conductivity values are understood to represent aqueous solutions lacking non-ionic organic polymers, and measured by devices that support linear accuracy.

In one or more of the preceding embodiments, methods employ a non-protein-precipitating salt characterized by having a conductivity of the salt in a range of from about 16 mS/cm to about 200 mS/cm. For reference, the conductivity of a physiological solution is about 12-15 mS/cm, so the specification of 16-160 is intended to indicate conductivities and corresponding salt concentrations greater than normal physiological levels.

In one or more of the preceding embodiments, nonionic organic polymer precipitation methods employ a non-precipitating salt characterized by having a conductivity of the salt in a range from about 20 to 140 mS/cm.

In one or more of the preceding embodiments, nonionic organic polymer precipitation methods employ a non-precipitating salt characterized by having a conductivity of the salt in a range from about 50 to 120 mS/cm.

In one or more of the preceding embodiments, nonionic organic polymer precipitation methods employ a non-precipitating salt characterized by having a conductivity of the salt in a range from about 60 to 100 mS/cm.

In one or more of the preceding embodiments, nonionic organic polymer precipitation methods employ a non-precipitating salt characterized by having a conductivity of the salt in a range from about 80 to 120 mS/cm.

In one or more of the preceding embodiments, a non-protein-precipitating salt is selected from the group consisting of sodium chloride, potassium chloride, sodium acetate, potassium acetate, sodium thiocyanate, potassium thiocyanate, and guanidine chloride, and combinations thereof.

In one or more of the preceding embodiments, more than one non-protein-precipitating salt may be present and the aggregate conductivity of the combined non-protein-precipitating salts may be in a range of from about 16 mS/cm to about 200 mS/cm.

In one or more of the preceding embodiments, the concentration of non-protein-precipitating salts is nominally constant during the precipitating and washing steps.

In one or more of the preceding embodiments, after precipitation, the precipitate is washed with a solution comprising nominally the same concentration of nonionic organic polymer and non-precipitating salt, and pH, as the solution in which the desired protein was initially precipitated.

In one or more of the preceding embodiments, after precipitation, the precipitate is washed with a solution comprising a precipitating salt at a concentration sufficient to maintain the desired product in a precipitated state, and the solution nominally lacks nonionic organic polymer. In a related embodiment, the precipitate may be washed again with a solution comprising a precipitating salt at a concentration sufficient to maintain the precipitate in a precipitated state, and the solution nominally lacks nonionic organic polymer. In a related embodiment, after precipitation and after the precipitate has been washed with a solution containing a nonionic organic polymer and a non-precipitating salt, the precipitate is further washed with a solution comprising a precipitating salt at a concentration sufficient to maintain the desired product in a precipitated state, and the solution nominally lacks nonionic organic polymer. In a related embodiment, the precipitate may be washed additional times.

In one or more of the preceding embodiments, precipitation with a nonionic organic polymer combined with a non-protein-precipitating salt is followed by a wash with a protein-precipitating salt at sufficient concentration to maintain the desired protein in a precipitated state.

In one or more of the preceding embodiments, precipitation with a nonionic organic polymer combined with a non-protein-precipitating salt, followed by a wash with a nonionic organic polymer and a non-protein-precipitating salt, is followed by a wash with a protein-precipitating salt at sufficient concentration to maintain the desired protein in a precipitated state.

In one or more of the preceding embodiments, methods further comprise processing in a subsequent chromatography step.

In one or more of the preceding embodiments, the desired protein, after washing with precipitating salt in the nominal absence of a nonionic organic polymer, and after resolubilization, may, without sample equilibration, be further purified by the method of anion exchange chromatography in void exclusion mode (Nian et al, J. Chromatogr. A 1282 (2013) 127-132).

In one or more of the preceding embodiments, the desired protein, after resolubilization, may be further purified by the method of apatite chromatography on a chromatography medium consisting of a hydroxyapatite, or a fluorapatatite, or a hybrid apatite, or a secondarily calcium-derived apatite, or other metal-derived apatite, such as zinc apatite, or copper apatite, or iron apatite, or another metal-derived apatite.

In one or more of the preceding embodiments, the desired protein, after resolubilization, may be further purified by the method of multimodal chromatography with a hydrophobic electropositive medium. In one such embodiment, the electropositive hydrophobic chromatography medium also contains residues that may mediate hydrogen bonding. In one such embodiment, the chromatography medium may be Capto adhere.

In one exemplary embodiment integrating numerous aspects of the disclosed methods, an IgG-containing cell culture harvest clarified by a chromatin-directed method is precipitated with 19% PEG-6000 in the presence of 600 mM NaCl and 20-50 mM Hepes or phosphate buffer at a pH of 7.0. The precipitate is sedimented and the supernatant removed, then the precipitate is washed with 19% PEG-6000 in the presence of 600 mM NaCl and 20-50 mM Hepes or phosphate buffer at a pH of 7.0. The supernatant is discarded and the precipitate is re-solubilized in 50 mM Tris, 1 M NaCl, pH 8.0 and applied to a column packed with Capto adhere. Residual PEG flows through the column and is thereby eliminated. The antibody is retained, and subsequently eluted by reducing the concentration of NaCl to 300 mM, with the effect of removing most of the aggregates.

In one exemplary embodiment integrating numerous aspects of the disclosed methods, an IgG-containing cell culture harvest clarified by a chromatin-directed method is precipitated with 19% PEG-6000 in the presence of 600 mM NaCl and 20-50 mM Hepes or phosphate buffer at a pH of 7.0. The precipitate is sedimented and the supernatant removed, then the precipitate is washed with 1.5 M ammonium sulfate, 20-50 mM in Hepes or phosphate buffer, at a pH of 7.0. The precipitate is sedimented, the supernatant removed, then the precipitate is washed again with 1.5 M ammonium sulfate, 20-50 mM in Hepes or phosphate buffer at a pH of 7.0. The precipitate is re-solubilized in Hepes or phosphate buffer at a pH of 7.0 and applied to a column packed with UNOsphere Q equilibrated to 20 mM Tris, pH 8.0 operated in void exclusion mode.

In one or more of the preceding embodiments, protein-precipitating salts comprise one selected from the group consisting phosphates, sulfates, citrates, and combinations thereof, including specific examples such as sodium sulfate, potassium-sulfate, ammonium sulfate, potassium phosphate, sodium citrate, potassium citrate, ammonium citrate.

In one or more of the preceding embodiments, protein-precipitating salts are combined with non-protein precipitating salts, in the substantial absence of a nonionic organic polymer.

In one or more of the preceding embodiments, the substantial absence of a protein-precipitating salt comprises the presence of only a sufficient amount to mediate pH control, wherein the sufficient amount is in a range of from about 5 mM to about 100 mM. In one or more of the preceding embodiments, the substantial absence of a protein-precipitating salt comprises the complete absence of a precipitating salt. In one or more of the preceding embodiments, the substantial absence of a precipitating salt comprises an intermediate concentration of precipitating salt or salts. This highlights the point that reference to a particular salt as a protein-precipitating salt does not mean that it is necessarily present at a concentration sufficient to precipitate the desired protein. Precipitating salts are understood to refer to so-called lyotropic or kosmotropic salts according to their position in the Hofmeister series of chaotropic and lyotropic ions. The term non-protein-precipitating salts is understood to refer to salts that generally do not precipitate proteins at any concentration. Such salts comprise ions that are chaotropic in the Hofmeister series, or within the mid-range of the series, but not among the salts generally classified as being lyotropic or kosmotropic.

In one or more of the preceding embodiments, the pH during the precipitating step is about 7 or in a range selected from the group consisting of (i) about 6.5 to about 7.5, (ii) about 5.5 to about 8.5, and (iii) about 4.0 to about 9.0.

In one or more of the preceding embodiments, the pH during the precipitating step is not adjusted. In a related embodiment, the pH of the precipitating step is not adjusted to within 1 pH unit of the isoelectric point of the desired protein. In a related embodiment, the pH during the precipitation step is not adjusted to within 0.5 pH units of the isoelectric point of the desired protein.

In one or more of the previous embodiments, the pH during the precipitation step may be adjusted to within 0.6 units of the isoelectric point of the desired protein, or within 0.7 units, or 0.8 units, or 0.9 units, or 1 unit, or 1.1 units, or 1.2 units, or 1.3 units, or 1.4 units, or 1.5 pH units, or 2.0 pH units, or within a greater interval from the isoelectric point of the desired protein.

In one or more of the previous embodiments, different stages of the process may utilize different pH values. In one embodiment, the pH value during high salt conditions may be very broad since the salt will suppress electrostatic interactions. This highlights the point that there is no need to adjust the pH to the isoelectric point of a desired protein.

In one or more of the previous embodiments, the pH at which a particular stage of the method is conducted may be selected according to its ability to enhance contaminant removal.

In one or more of the previous embodiments, the pH at which a particular stage of the method is conducted may be selected according to its ability to enhance the ability of electropositive materials in the system to bind contaminants.

In one or more of the preceding embodiments, the desired protein is an IgG, IgM, IgA, IgD, IgE, Fc-fusion protein, a non-antibody protein, a clotting protein, a complex of a clotting protein with a co-factor.

In one or more of the preceding embodiments, the desired protein is partially purified.

In one or more of the previous embodiments, the antibody is an IgG. In one such embodiment, the antibody is a monoclonal IgG. In a closely related embodiment, the desired protein comprises an IgG fragment, such as an Fc-fragment that is an integral component of a so-called Fc-fusion protein.

In one or more of the previous embodiments, the method is used to purify a non-IgG antibody. In one such embodiment the antibody is an IgM.

In some embodiments, the desired protein may be an antibody. In some such embodiments, methods of purifying the antibody may further comprise contacting a cell culture harvest or a protein preparation comprising at least one antibody with at least one fatty acid having 7 to 10 carbon atoms to form a mixture, optionally contacting the mixture with allantoin, contacting the mixture with one or more functionalized solid and/or soluble substrates to form a mixture, wherein the one or more functionalized substrates comprise a cationic functional group, a metal binding functional group, or both, wherein the metal binding functional group comprising a nitrogen-containing moiety selected from the group consisting of (1) a polyamine, (2) an imine, (3) an N-heterocycle, (4) an amino acid, (5) an N-hydroxyamide, (6), an arylamine, and combinations thereof, and separating solid materials after contacting the mixture with the one or more solids to provide a solution comprising the IgG antibody.

In some such embodiments, methods may further comprise contacting the cell culture harvest with allantoin.

In one or more of the preceding embodiments, allantoin may be present at a concentration in a range selected from the group consisting of: (a) from about 0.6 to about 30%, (b) from about 1 to about 10%, and (c) from about 1 to about 2%.

In one or more of the preceding embodiments, allantoin is in a range from a non-zero amount up to about 0.6%.

In one or more of the preceding embodiments, a total amount of the one or more functionalized substrate's is a volumetric proportion of the total volume of about 0.01%, 0.05%, 0.1%, 0.25%, 0.5%, 1%, 2%, 5%, 10%, 20%, or intermediate values in between.

In one or more of the preceding embodiments, the at least one fatty acid and the one or more functionalized substrates are disposed in a single vessel.

In one or more of the preceding embodiments, the one or more functionalized substrates are disposed in a device that permits the passage of fluid while preventing the passage of solid materials therethrough.

In one or more of the preceding embodiments, the methods further comprise contacting the solution with functionalized solids disposed in a device.

In one or more of the preceding embodiments, the device that permits the passage of fluid while preventing the passage of solids therethrough comprises a porous material selected from the group consisting of a membrane, a monolith, a woven material, a crystalline material, a gelatinous material, a column of packed particles, and combinations thereof.

In one or more of the preceding embodiments, solid materials present after contacting a cell culture harvest with the at least one fatty acid or at the separating step, are removed by sedimentation or sedimentation following centrifugation.

In one or more of the preceding embodiments, solid materials present after contacting a cell culture harvest with the at least one fatty acid or at the separating step, are removed by filtration.

In one or more of the preceding embodiments, filtration comprises membrane filtration or depth filtration.

In one or more of the preceding embodiments, the membrane filtration or depth filtration comprises a contact surface that is functionalized.

In one or more of the preceding embodiments, the first contacting step is preceded by partial purification of the IgG antibody.

In one or more of the preceding embodiments, the cell culture harvest or protein preparation contains cells, and optionally resides in the bioreactor within which cell culture production was performed.

In one or more of the preceding embodiments, the cell culture harvest or protein preparation does not contain cells.

In one or more of the preceding embodiments, the protein preparation is a naturally occurring biological fluid.

In one or more of the preceding embodiments, the at least one fatty acid comprises a general structural formula of $CH_3(CH_2)_n COOH$.

In one or more of the preceding embodiments, the at least one fatty acid comprises enanthic (heptanoic) acid, caprylic (octanoic) acid, octenoic acid, pelargonic (nonanoic) acid, nonenoic acid, or capric (decanoic) acid.

In one or more of the preceding embodiments, the at least one fatty acid is nonanoic acid.

In one or more of the preceding embodiments, the at least one fatty acid is present at a concentration in a range selected from the group consisting of: (a) from about 0.05 to about 5%, (b) from about 0.1 to about 1.0%, (c) from about 0.2 to about 0.4%, and (d) from about 0.1 to 0.2%.

In one or more of the preceding embodiments, the mixture may contain a surfactant.

In one or more of the preceding embodiments, a surfactant contained in the mixture may be nonionic, or zwitterionic, or cationic.

In one or more of the preceding embodiments, a cationic surfactant contained in the mixture may be cetyltrimethylammonium bromide.

In one or more of the preceding embodiments, cetyltrimethylammonium bromide may be present at a concentration ranging from about 0.001% to 0.05%, or from about 0.005% to 0.025%, or from about 0.0075% to about 0.01%.

In one or more of the preceding embodiments, the one or more functionalized substrates comprises at least one charge configuration selected from the group consisting of anionic, cationic, or zwitterionic.

In one or more of the preceding embodiments, the one or more functionalized substrates comprises one substrate with the metal binding functional group and a separate substrate that is cationic.

In one or more of the preceding embodiments, the metal binding functional group is cationic.

In one or more of the preceding embodiments, the metal binding functional group is selected from the group consisting of tris(2-aminoethyl)amine, diethylenetriamine, triethylenetriamine, tetraethylenepentamine, polypropyleneimine tetramine, poly(amidoamine) (PAMAM) dendrimer, deferoxamine (desferioxamine), arginine, histidine, histamine, imidazole, and combinations thereof.

In one or more of the preceding embodiments, the metal binding functional group is a compound of formula I:

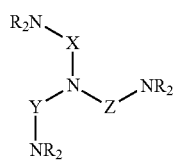

I wherein each incidence of R is independently hydrogen or $C_1$-$C_4$ alkyl, with the proviso that at least one R is the site of attachment to a solid support, optionally via a linker; and each of X, Y, and Z are independently $(CH_2)_n$, where n is an integer from 2 to 6, wherein a $CH_2$ group is optionally replaced by O, or NH.

In one or more of the preceding embodiments, the cationic chelating agent is tris(2-aminoethyl)amine.

In one or more of the preceding embodiments, the one or more functionalized solid or soluble substrates comprises one substrate with the metal binding functional group and a separate substrate that is anionic.

In one or more of the preceding embodiments, the metal binding functional group is anionic.

In one or more of the preceding embodiments, the metal binding functional group is selected from the group consisting of iminodiacetic acid, nitriloacetic acid, glutamic acid, aspartic acid, aminophenyl phosphate, and combinations thereof.

In one or more of the preceding embodiments, the anionic chelating agent is iminodiacetic acid.

In one or more of the preceding embodiments, the one or more functionalized solid or soluble substrates comprises one substrate that is cationic and a separate substrate that is anionic.

In one or more of the preceding embodiments, the antibody is an IgG or IgM antibody.

In some embodiments, there are provided methods for purifying an antibody comprising contacting a cell culture harvest or protein preparation with at least one fatty acid having 8 to 10 carbon atoms to form a mixture, contacting the mixture with allantoin, and separating solid materials after contacting the mixture with allantoin to provide a solution comprising the antibody. In some such embodiments, the method further comprises contacting the solution with at least one chemically functionalized solid or soluble substrate.

In some such embodiments, the at least one chemically functionalized solid comprises tris(2-aminoethyl)amine.

In one or more of the preceding embodiments, allantoin is present at a concentration in a range selected from the group consisting of (a) from about 0.6 to about 30%, (b) from about 1 to about 10%, (c) from about 1 to about 5%, and (d) from about 1 to about 2%.

In one or more of the preceding embodiments, allantoin is in a range from a non-zero amount up to about 0.6%.

In some embodiments, there are provided method for the purification of a desired protein from a protein preparation comprising conditioning the protein preparation by treatment with soluble organic multivalent ions, immobilized organic multivalent ions, or both, optionally in the presence of supersaturated allantoin, thereby removing at least 90% of chromatin, then (1) precipitating the desired protein with a non-ionic organic polymer in the presence of non-protein-precipitating salts at greater than physiological concentration to provide a precipitate of the desired protein, or (2) precipitating the desired protein with a nonionic organic polymer in the absence of non-precipitating salts at greater than physiological concentration to provide a precipitate and subsequently washing the precipitate with a nonionic organic polymer in the presence of non-protein-precipitating salts at greater than physiological concentration, wherein the precipitating or washing step is optionally carried out in the substantial absence of a protein-precipitating salt, and optionally without adjusting the pH of the desired protein to a value within 0.5 pH units of the isoelectric point of the desired protein, and optionally washing the precipitate with a protein-precipitating salt in the absence of a non-ionic organic polymer, where in the precipitating salt is present at a sufficient concentration to keep the desired protein in a precipitated state.

"Physiological salts" comprise a mixture, principally of sodium and potassium chloride, but, also lower levels of many other salts. It will be generally understood that the amount of "physiological salts" is estimated to correspond to an equivalent total salt concentration of about 0.15 M NaCl. Thus, as used herein, an amount of non-protein-precipitating salts "greater than physiological concentration" includes salt concentrations greater than about 0.15M, or greater than about 0.2 M, or greater than about 0.3 M, or greater than about 0.5M and so on, including any amount in between and fractions thereof. That is, the amount can be any amount greater than what is typical under physiological conditions. In some embodiments, the concentration may be in a range from about 0.2 M to about 2.0M, including any amount in between and fractions thereof.

Thus, for example, methods disclosed herein may comprise the steps of (1) precipitating the desired protein with a non-ionic organic polymer in the presence of non-protein-precipitating salts at concentration greater than about 0.2M to provide a precipitate of the desired protein; or (2) precipitating the desired protein with a nonionic organic polymer in the absence of non-precipitating salts at a concentration greater than about 0.2M to provide a precipitate and subsequently washing the precipitate with a nonionic organic polymer in the presence of non-protein-precipitating salts at a concentration greater than about 0.2M, wherein the precipitating or washing step is optionally carried out in the substantial absence of a protein-precipitating salt, and optionally without adjusting the pH of the desired protein to a value within about 0.5 pH units of the isoelectric point of the desired protein, and optionally washing the precipitate with a protein-precipitating salt in the absence of a non-ionic organic polymer, where the precipitating salt at a sufficient concentration to keep the desired protein in a precipitated state.

In some embodiments, conditioning the protein preparation with organic multivalent ions comprises contacting the sample with an electropositive organic additive. In some such embodiments, the electropositive organic additive is one or more from the group of soluble cations consisting of methylene blue, ethacridine, chlorhexidine, benzalkonium chloride, cetyl trimethyl ammonium bromide.

In some embodiments, the electropositive organic additive is one or more from the group consisting of a cation that is insoluble due to its immobilization on a solid surface, including a primary amino group, a secondary amino group, a tertiary amino group, a quaternary amino group, a complex cation containing more than one positive charges conferred by one or more types of amino groups.

In some embodiments, the electropositive organic additive is 2(aminoethyl) amine (TREN) immobilized on a solid.

In some embodiments, conditioning the protein preparation with organic multivalent cations comprises contacting the sample with an electronegative organic additive.

In some embodiments, the electronegative organic additive is one or more from the group of soluble anions consisting heptanoic acid, octanoic acid, octenoic acid, nonanoic acid, nonenoic acid, decanoic acid, methyl blue.

In some embodiments, the electronegative organic additive is one or more from the group consisting of an anion that is insoluble due to its immobilization on a solid surface, including a phospho group, a carboxyl group, a sulfo group, a complex anion containing more than one negative charge conferred by one or more types of negatively charged groups.

In some embodiments, the electronegative organic additive is iminodiacetic acid, nitriloacetic acid, or a combination of the two.

In some embodiments, an electronegative organic additive or electropositive organic additive has a 1:1 affinity for metal ions.

In some embodiments, allantoin, if included, is present in a supersaturating concentration in a range from the group consisting of 0.6 to 50%, 0.7 to 20%, 0.8 to 10%, 0.9 to 5%, 1 to 2%, or an intermediate value.

In some embodiments, the nonionic organic polymer is polyethylene glycol (PEG).

In some embodiments, the polymer size is in a range from the group consisting of 1000 to 12,000 Daltons (D), from 2000 to 8,000 D, 3000 to 6000 D, or an intermediate size such as one from the group consisting of 1500 D, 3500 D, 4000 D, 6000 D.

In some embodiments, the non-protein-precipitating salt may include one selected from the group consisting of sodium acetate, potassium acetate, sodium chloride, potassium chloride, and combinations thereof.

In some embodiments, one or more non-protein-precipitating salts may be added to a conditioned cell culture harvest in an amount sufficient that the salt concentration after addition of the nonionic organic polymer is greater than physiological concentration by an increment ranging from about at least 0.05M to about 2.0M. Thus, the increment can be greater than at least about 0.05, 0.1, 0.2, 0.3, 0.4, 0.5, 0.6, 0.7, 0.8, 1.0, 1.5, and 2.0 M, or even more, including any value in between and fractions thereof. In some embodiments, the concentration may be in a range from about 0.5 to about 1.5 M.

In some embodiments, an individual salt or a combination of non-protein-precipitating salts is added to a cell culture harvest to elevate the overall salt concentration above the normal physiological salt content, and the excess of non-protein-precipitating salt is maintained in conjunction with the addition of the nonionic organic polymer. In some embodiments, the concentration may be greater than an increment in a range from about 1.2M to about 1.8M. In some embodiments, the increment is about 1.2 M, 1.3 M, 1.4 M, 1.5 M, 1.6 M, 1.7 M, or about 1.8M. In some embodiments, the concentration may be in a range from about 0.5 to about 1.5 M.

In some embodiments, one or more non-protein-precipitating salts may be added to a protein preparation in conjunction with addition of the nonionic organic polymer so that the final salt concentration is greater than normal physiological concentration by an increment of at least 0.05M. In some embodiments, the concentration may be greater than an increment in a range from about 1.2M to about 1.8M. In some embodiments, the increment is about 1.2 M, 1.3 M, 1.4 M, 1.5 M, 1.6 M, 1.7 M, or about 1.8M. In some embodiments, the concentration may be in a range from about 0.5 to about 1.5 M.

In some embodiments, one or more non-protein precipitating salts may be added so that the net salt concentration of the protein preparation is higher than the normal physiological value in a range from the group consisting of 200 mM to 2 M, 300 mM to 1.5 M, 400 mM to 1 M, 500 mM to 800 mM, or an intermediate value.

In some embodiments, non-precipitating salts at a concentration of at least 0.2M are included in a wash solution to maintain an excess already existing in the precipitate.

In some embodiments, when non-precipitating salts are absent in an initial precipitation step, they are included in at least one washing step.

In some embodiments, a precipitate may be washed with one or more precipitating salts at a concentration sufficient to maintain the desired protein in a precipitated state. In some such embodiments, the precipitating salts are employed in the absence or substantial absence of nonionic organic polymer, such as PEG. Those skilled in the art will appreciate that at sufficiently high concentrations the two agents may be incompatible because PEG may separate as a distinct organic layer. Nonetheless, there are viable conditions where low concentrations of one agent may be added to a higher concentration of the other.

In some embodiments, one or more precipitating salts may be selected from the group consisting of sodium sulfate, potassium sulfate, ammonium sulfate, sodium phosphate, potassium phosphate, ammonium phosphate, sodium citrate, potassium citrate, ammonium citrate and combinations thereof.

In some embodiments, the desired protein is a naturally occurring protein, a recombinant protein, an antibody, a monoclonal antibody, an IgG antibody, or an IgM antibody.

In some embodiments, the preparation is a bodily fluid, milk, plasma, serum, or a cell culture harvest.

Terms are defined so that the embodiments may be understood more readily. Additional definitions are set forth throughout the detailed description.

"PEG precipitation" refers to a purification method in which a desired protein becomes insoluble at a critical concentration of PEG, and forms solid precipitates that can be removed from solution by filtration or centrifugation, leaving the majority of contaminants in the remaining liquid (supernatant). The supernatant is traditionally removed by filtration or centrifugation followed by decantation. In most cases the precipitate is washed byre-suspending the precipitate one or more times with PEG-containing buffer to dilute out contaminants that reside in the interstices of the precipitate, especially after centrifugation. Wash steps are traditionally repeated one or more times, frequently with buffers of different composition, though always with sufficient PEG to keep the desired protein precipitated. The precipitated protein is finally re-solubilized in a low-or-no PEG buffer. Traditionally, the desire protein may be re-precipitated and re-solubilized one or more times to further increase the purity of the desired protein.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Host contaminant" or "Host cell contaminant" refers to biomolecules that are produced by the cells in which the product of interest is gown. The term may include various classes of host contaminants, such as host proteins and host DNA.

"Host protein" or "Host cell protein" or "HCP" refers to proteins that are produced by the cells in which the product of interest is grown. Such proteins represent one class of contaminants that must be removed from the product of interest.

"Antibody" refers to an immunoglobulin of the class IgG, IgM, IgA, IgD, or IgE derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety, or immunoconjugates created by synthetic linkage of an IgG to another functional moiety, including another antibody, an enzyme, a fluorophore or other signal generating moiety, biotin, a drug, or other functional moiety.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the methods include but are not limited to polyethylene glycol (PEG), polypropylene glycol, polyvinylpyrrolidone (PVP), and others. PEG has a structural formula $HO-(CH_2-CH_2-O)_n-H$. Examples include, but are not limited to compositions with an average polymer molecular weight ranging from less than 100 to more than 10,000 daltons.

"Anion exchange particle" or "electropositive particle" refers to a porous or nonporous particle, the surface of which is dominated by positive charge. Particle size may range from less than 50 nm to more than 200 microns. The particles may comprise a polymeric, crystalline, or ceramic structure that may also incorporate features that allow them to be sequestered by means that do not involve or interfere with their ability to perform the methods disclosed herein, but may provide some overall enhancement. Examples include but are not limited to features that confer low density that enables flotation, high density that enhances rapid sedimentation, and/or magnetism that enables their collection in a magnetic field. Electropositivity may be conferred by chemical groups including but not limited to weak anion exchange groups like amino, ethylene diamino, diethylaminoethyl, polyallylamine, polyethyleneimine; strong anion exchange groups, such as quaternary amino groups; combined weak-strong exchangers, such as polylysine, polyarginine, or Tris(2-aminoethyl)amine, diethylenetriamine, triethylenetetramine, tetraethylenepentamine, polypropyleneimine tetraamine, PAMAM dendrimer (ethylenediamine core), or any combinations of the foregoing. Secondary functionalities that create a mixed chemical character on a positively charged membrane may consist of negatively or positively charged groups, hydrophobic groups, pi-pi bonding groups, hydrogen-bonding groups, or metal-chelation groups. The secondary functionalities may exist on the membrane surfaces as an inadvertent byproduct of the manufacturing materials or process by which the particles are synthesized, or they may be present by deliberate design. The concentration of secondary functionalities may range from less than 1 milliequivalent per mL of particles, to more than 100 milliequivalents per mL.

"Organic multivalent ion" refers to an organic molecule, ion or salt of natural or synthetic origin that embodies at least one charge and at least one additional chemical functionality, thus rendering it multivalent. In certain embodiments, an organic multivalent ion the at least one additional chemical functionality is an additional charge such that the organic multivalent cation bears two or more like or differing charges. The organic multivalent ion may bear a net positive, net negative, or net neutral charge. Where the organic multivalent ion is net positive it may be provided together with anions such as chlorides, bromides, sulfates, organic acids, lactates, gluconates, and any other anion not incompatible with the method. In certain embodiments certain of the positive charges of the organic multivalent ion are supplied by amine, imine or other nitrogen moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of positively charged organic multivalent ions in certain embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris (2-aminoethyl)amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates); also thiazins such as methylene blue (also known as basic blue 9), analogs and variants thereof, including methylene green (also known as basic green 5), Lauth's violet (also known as thionin), methylene azure A, methylene azure B, and methylene azure C. Where the organic multivalent ion is net negative it may be provided together with cations such as sodium or potassium; or any other cation not incompatible with the method. In certain embodiments certain of the negative charges of the organic multivalent ion are supplied by carboxyl, phospho, or sulfo moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of negatively charged organic multivalent ions in certain embodiments include but are not limited to the fatty acids such as octanoic acid, octenoic acid, nonanoic acid, nonenoic acid, electronegative polymers, and salts thereof (e.g. chlorides, bromides, sulfates, lactates, gluconates), and aryl compounds such as methyl blue.

"Protein-precipitating salt" or "antibody-precipitating salt" or "IgG-precipitating salt" refers to a salt that embodies the ability to mediate precipitation of a desired protein. Common examples include sodium or ammonium sulfate, sodium or potassium citrate, sodium or potassium phosphate. Such salts are commonly referred to as kosmotropic salts.

"Non-protein-precipitating salt" or "non-antibody-precipitating salt" or "non-IgG-precipitating salt" refers to a salt that lacks the ability to mediate precipitation of a desired protein, and may embody the ability to increase solubility of a desired protein. Common examples include but are not limited to sodium or potassium chloride, sodium or potassium acetate, sodium or potassium thiocyantate, or guanidinium chloride. Some such salts are commonly referred to as chaotropic salts, while others are neither referred to as chaotropic nor kosmotropic.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

Development of an IgG purification process serves as a useful example to illustrate the steps of customizing the disclosed methods to a particular desired protein. Development begins with selecting a clarification method to remove 90% or more of the chromatin from a cell culture harvest. One useful starting point is to add allantoin in an amount of 1% w/v to the harvest, followed by the addition of caprylic acid in an amount of 0.4% w/v. The pH of the mixture is adjusted to 5.2 and mixed for 2 hours at room temperature. Positively charged metal affinity particles, such as BioWorks TREN high are equilibrated to pH 5.2 then added to the mixture in an amount of 5% v/v, and incubated stirring for 4 hours. Solids are then removed by any expedient method. The method may be followed by passing the supernatant through a depth filter, the fluid contact surfaces of which bear electropositive ligands. Conductivity, pH, and concentrations of reactants may be subsequently refined if desired. The clarified IgG preparation now substantially devoid of chromatin and chromatin catabolites, is precipitated by addition of PEG-6000 to a final concentration of 19%. NaCl is also added in an amount of 600 mM, bringing the net salt concentration (sample+added NaCl) to a presumptive concentration of about 750 mM. pH is about 7 (6.8 to 7.2) conferred and controlled by 20-50 mM Hepes, or by sodium or potassium phosphate, pH 7. These conditions can be further refined-if desired, including by substitution with other buffering substances. The precipitate is collected by centrifugation or filtration, and the supernatant discarded. The precipitate is re-suspended in 19% PEG-6000, 750 mM NaCl, 20-50 mM Hepes or phosphate, pH 7, then the precipitate is re-collected and the supernatant discarded. One option at this point is to wash the precipitate again with a precipitating salt at a concentration that keeps the IgG in a precipitated state. This has the effect of removing residual PEG. The precipitate can then be re solubilized and purified further by one or more additional fractionation methods, if desired. One option is to apply the sample to a column of UNOsphere Q operated in void exclusion mode, where the column is equilibrated to 50 mM Tris, pH 8.2. Alternative chromatography methods are known and it is within the purview of a person of ordinary skill in the art to choose a suitable method or methods, and develop the conditions to operate them.

A different approach to development of an IgG purification illustrates some of the alternatives that may be considered. As in the previous general example, development begins with selecting a clarification method to remove 90% or more of the chromatin from a cell culture harvest. One useful starting point is to add allantoin in an amount of 1% w/v to the harvest, followed by the addition of ethacrdine acid in an amount of 0.025% w/v. The pH of the mixture is adjusted to 7.5 and mixed for 2 hours at room temperature. Positively charged metal affinity particles, such as BioWorks TREN high, are equilibrated to pH 7.5 then added to the mixture in an amount of 4% v/v, while negatively charged hydrophobic particles such as Bio-Rad MacroPrep tbutyl are added in an amount of 1% v/v, and incubated stirring for 4 hours. Solids are then removed by any expedient method. The method may be followed by passing the supernatant through a depth filter, the fluid contact surfaces of which bear electropositive ligands. Conductivity, pH, and concentrations of reactants may be subsequently refined if desired. The clarified IgG preparation now substantially devoid of chromatin and chromatin catabolites, is precipitated by addition of PEG-6000 to a final concentration of 19%. NaCl is also added in an amount of about 850 mM, bringing the net salt concentration (sample+added NaCl) to a presumptive concentration of about 1M. pH is about 7 (6.8 to 7.2) conferred and controlled by 20-50 mM Hepes, sodium or potassium phosphate, pH 7. These conditions can be further refined if desired. The precipitate is collected by centrifugation or filtration and the supernatant discarded. The precipitate is suspended in 19% PEG-6000; 1 M NaCl, 20-50 mM Hepes or phosphate, pH 7, then the precipitate is re-sedimented and the supernatant discarded. The precipitate can then be re-solubilized, for example with 50 mM phosphate, 1 M NaCl, pH 7.2, and purified further by application to a column of Capto adhere equilibrated to the same conditions, if desired. The purified IgG may then be eluted by reducing the NaCl concentration to 300 mM. Alternative chromatography methods are known and it is within the purview of a person of ordinary skill in the art to choose a suitable method or methods, and develop the conditions to operate them.

Many variations of the above processes may be, considered, including simplifications were certain components are omitted, such as allanotoin, or certain components are varied, such as replacing TREN particles with Dowex AG1X2 or others, such as replacing MacroPrep t-butyl with Chelex 100 or others, contacting the mixture with these particles in a column format instead of a batch format as described above, or where the electropositive and/or electropositive organic ions are resident on the surfaces of other solids such as membranes, fibers, hydrogels, or other physical supports. Examples of such variations and more are discussed in Appendices A-D.

Adaptation of the disclosed method will frequently involve the addition of salts or other additives during clarification to prevent the loss of desired product through its strong interactions with soluble or insoluble electropositive or electronegative organic ions.

Since the results obtained by using the methods disclosed herein are a function of chemical processes, it is to be understood that all physical formats are capable of achieving similar results, but may do so with different levels of efficiency, different fluid volumes, and different time intervals. It is within the purview of the person of ordinary skill to determine how to effectively configure the methods to a particular application.

EXAMPLES

Example 1

Selection of NaCl concentration for conducting precipitation. 1 L of cell culture supernatant containing 1.2 g/L of monoclonal anti-HER2 IgG was clarified by centrifugation and membrane filtration. The isoelectric point of this antibody is about 8.6. 1% allantoin was added, followed by the addition of ethacridine at a final concentration of 0.025%. Solids were removed by filtration. Equal proportions of positively charged metal affinity particles (BioWorks TREN hi-sub), negatively charged metal affinity particles (Chelex-100), and positively charged hydrophobic particles (Dowex AG1x2 400-mesh) were combined. 20 mL of the particle mixture was packed into a 1.6×10 cm column, equilibrated to roughly physiological conditions, and the sample passed over the column at a linear flow rate of 300 cm/hr. The treated HER2 contained 165,663 ppm host cell protein contamination. It was precipitated at pH 7 in a solution of 18% PEG-6000. The supernatant was removed by filtration through an uncharged membrane with average 0.22 micron pores. The precipitate was resuspended in 50 mM Hepes, 18% PEG, pH 7.0, and the supernatant was again removed by filtration on the same membrane. The antibody was then solubilized in 50 mM Hepes, pH 7.0. In a parallel experiment, NaCl was added to the original sample to create a salt concentration equivalent to 200 mM. 200 mM NaCl was also added to the resuspension buffer. In additional parallel experiments, the NaCl concentrations were raised to 400, 800, and 1000 mM NaCl. The concentration of contaminating host cell proteins was measured in the resolubilized antibody from each experiment. Those levels were as follows: no added NaCl, 16,544 ppm; 200 mM NaCl, 1,984 ppm; 400 mM NaCl, 605 mM NaCl; 800 mM NaCl, 50 ppm; 1000 mM NaCl, 32 ppm.

Example 2

The experiment from example 1 at 800 mM NaCl was repeated except that no salt was added to the original sample. The resolubilized antibody contained 155 ppm host cell protein. In subsequent experiments where exposure to the resuspension buffer was extended or repeated, the concentration of contaminating host protein was reduced to about 70 ppm. This highlights the point that performance is improved when the initial precipitation step is conducted at elevated salt concentration.

Example 3

The basic form of example 2 with no salt added to the original sample, but including extended exposure to 800 mM NaCl during the wash of the resuspended precipitate. The precipitated IgG was subsequently washed with 50 mM Tris, 18% PEG, pH 8.0 before the antibody was solubilized in 50 mM Tris, pH 8.0. Host protein contamination was reduced to 88 ppm; still inferior to the results obtained when the initial precipitation was conducted at high salt.

Example 4

The experiment of example 3 was repeated except beginning with cell-containing cell culture harvest. Results were essentially unchanged, demonstrating that the benefits of the conditioning method apply to both cell-containing and cell-free protein preparations.

Example 5

The basic form of example 3 was repeated except that IgG was resolubilized with 1 M NaCl, 50 mM Hepes, pH 7.0; then applied to a 10 mL column of Capto adhere, a hydrophobic anion exchanger equilibrated to the same conditions, then eluted with a descending gradient of 50 mM Hepes, pH 7.0. Residual PEG flowed through the column upon sample application and was thereby eliminated. The IgG was eluted in the gradient. Host protein contamination in the eluted IgG was less than 1 ppm. This example highlights the ability of the methods disclosed herein to achieve extraordinary antibody purification of conditioned IgG in only two fractionation steps. It will be understood that the ability of the methods disclosed herein to achieve such low levels of host protein contamination enables many such 2-step, procedures.

Example 6

The basic form of example 3 was repeated except that hydrophobic electropositive porous particles in the form of Dowex AG1x2 were introduced at a volumetric ratio of 2% immediately before the IgG was resolubilized. Host protein contamination was reduced to 21 ppm. Antibody recovery was 90%. In a parallel experiment, the Dowex particles were substituted with particles of UNOsphere Q. Host protein reduction was the same but antibody recovery was 95%.

Example 7

The basic form of example 6 was repeated except the salt concentration of clarified cell supernatant was raised to 1 M NaCl. Anion exchange particles in the form of UNOsphere Q were added in a proportion of 4% v/v. PEG-6000 in 50 mM Tris, 1 M NaCl to a final concentration of 19% PEG to precipitate the antibody. The supernatant was removed by filtration through a 0.22 micron nonionic membrane. The precipitate and particles were resuspended in 19% PEG-6000, 1 M NaCl, 50 mM Tris, pH 8.0, and the supernatant removed again by filtration. The precipitate and particles were then resuspended in 19% PEG, 50 mM Tris, pH 8.0, incubated stirring for 15 minutes, then the supernatant removed by filtration through the same filter. This wash was repeated then the antibody was solubilized with 50 mM Tris, pH 8.0. The resolubilized antibody and electropositive particles were mixed gently for 30 minutes to provide an opportunity for acidic host protein to bind to the particles, then the antibody solution was filtered through the membrane, leaving the particles behind. Host protein concentration of the antibody was 18 ppm. Antibody recovery was 93%.

Example 8

A series of experiments was conducted in which IgG purification and recovery were evaluated in a 2-dimensional matrix evaluating PEG-6000 concentrations of 16, 18, 20, and 22% versus NaCl concentrations of 0.0, 0.5, 1.0, 1.5, and 2.0 M. The source material was IgG-containing supernatant that was clarified exclusively by microfiltration. IgG recovery, purity, and reproducibility, and variation across PEG concentration were best at about 1 M NaCl. Purity was about the same at 1.5 M, but recovery was compromised. Recovery was slightly better at 0.5 M NaCl, but purity was lower than 1.0 M. Both purity and recovery were severely compromised in the absence of NaCl and at 2.0 M NaCl.

Example 9

The integrated method for purification of IgM. 1 L of cell culture supernatant containing 120 mg/L of monoclonal IgM clone 529 was clarified by centrifugation and membrane filtration. The isoelectric point of this antibody is about 6.0. Solid sodium chloride was added to achieve a final conductivity of 25 mS/cm. 1% allantoin was added, followed by the addition of ethacridine at a final concentration of 0.025%. Solids were removed by filtration. Equal proportions of strong anion exchange particles (Macroprep High-Q), negatively charged metal affinity particles (Chelex-100), and strong cation exchange charged particles (Macroprep High-S) were combined. 20 mL of the particle mixture was packed into a 1.6×10 cm column, equilibrated to roughly physiological conditions, and the sample passed over the column at a linear flow rate of 200 cm/hr. The treated HER2 contained 165,663 ppm host cell protein contamination. In a control experiment, the antibody was purified by precipitation with 13% PEG-6000 and a wash at a conductivity of 25 mS/cm. Remaining host protein contamination was 1383 ppm. In a parallel experiment, the antibody was purified by the same means but at a conductivity of 47 mS/cm. Remaining host protein contamination was 69 ppm. Subsequent purification by anion exchange and cation exchange chromatography reduced host protein concentration to less than 3 ppm.

Example 10

An IgG-containing cell culture harvest containing 275, 357 ppm host cell proteins, 5283 ppm DNA, and 13.96% aggregates was conditioned by addition of 1% allantoin, then 0.025% ethacridine, then mixed for 15 minutes. An equal mixture of MacroPrep High Q, MacroPrep High S, Macroprep tButyl, and Chelex-100 (Bio-Rad Laboratories), equilibrated in advance by washing with 50 mM HEPES, 100 mM NaCl, pH 7.0. Equilibrated mixed particles were added to the impure IgG preparation in an amount of 2% (v:v), then mixed overnight at 4-8 degrees C. Solids were removed by microfiltration. 1.25 mg of starch coated 200 nm magnetic particles were added to 20 mL of the conditioned impure IgG preparation. 20 mL of 36% PEG-6000 in 1.6 M NaCl, 50 mM HEPES, pH 7.0 was added gradually while mixing on a vortex mixer at 500 rpm to produce a final concentration of 18% PEG-6000 and 0.8 M NaCl. Vortex mixing was continued for 30 minutes, then the IgG-loaded particles were collected magnetically. The IgG-loaded particles were washed with fresh 50 mM HEPES, 0.8 M NaCl, pH 7.0, and the wash solution was removed. The wash buffer was removed and the particles were washed again in the same manner. The wash buffer was removed, and the antibody was resolubilized in 50 mM HEPES, 1 M NaCl, pH 7. A 1 mL column packed with an electropositive-hydrophobic chromatography medium (Capto adhere, GE Healthcare) and equilibrated to the same conditions. The solubilized IgG was applied to the column, where the IgG bound and some contaminants were understood to have bound, while residual PEG bind. A 5 column volume wash with equilibration buffer was then applied to more thoroughly eliminate unbound components from the system. The IgG was eluted with a 10 column volume linear gradient ending at 50 mM HEPES, 300 mM NaCl, pH 7.0. Purification performance is indicated by the following Table, where post-con indicates post-conditions, post-NP indicates post nanoparticles, and post-CA indicates post Capto adhere. The left-hand value under recovery indicates recovery for that step, while the right-hand value indicates cumulative recovery for previous steps plus that step. bld indicates below limit of detection. For more details refer to Gagnon et al 2014 supra:

| Step | HCP (ppm) | DNA(ppm) | Aggregates (%) | Recovery % |
|---|---|---|---|---|
| Harvest | 275,357 | 5,283 | 13.96 | 100/100 |
| Post-con. | 91,275 | 9 | 4.88 | 98/98 |
| Post-NP | 441 | bld | 3.59 | 87/84 |
| Post-C | 2 | bld | <0.05 | 81/69 |

Example 11

An IgG-containing cell culture harvest containing 176,244 ppm host protein contaminants and 19% aggregates was conditioned by addition of 1% allantoin, 4% electropositive metal affinity particles (TREN 40 high, Bio-Works), mixed for 4 hours at room temperature. A sample removed for analysis showed reduction of host proteins to 90,259 ppm, and aggregates to 1.2%. The pH was reduced to 5.2, 0.5% caprylic acid was added, and the mixture incubated for 2 hours. A sample removed for analysis showed host proteins at 1,758 ppm and aggregates at about 0.4%. Solids were removed through an electropositive depth filter (Sartorius PC1). Host proteins were reduced to 135 ppm and aggregates to less than 0.05%. The antibody was purified by precipitation in 18% PEG-6000 at pH 7.0. The precipitate was then washed with 1.8 M ammonium sulphate to remove PEG, then the antibody was resolubilized in 50 mM. Hepes, pH 7.0. Host protein was reduced to 32 ppm. After application to an anion exchange chromatography column (UNOsphere Q, Bio-Rad) operated in void exclusion mode at 50 mM Tris, pH 8.0, host protein was reduced to less than 1 ppm. A parallel experiment differing only in the PEG precipitation being conducted in the presence of 800 mM NaCl reduced host protein to less than 1 ppm. The anion exchange step reduced host protein and aggregates to an undetectable level. The method of anion exchange chromatography in void exclusion mode is described by R. Nian et al (J. Chromatogr. A 1282 (2013) 127-132).

Example 12

An IgG-containing cell culture harvest containing 286,010 ppm host protein contaminants and 23% aggregates was conditioned by addition of 1% allantoin and 0.025% ethacridine, and incubated stirring at room temperature for 1 hour. A 1:1:1 mixture of particles (Chelex-100, MacroPrep tButyl, Macroprep High Q, Bio-Rad) were mixed, equilibrated to physiological conditions, and settled mixed particles were added to the harvest in a combined amount of 5%, then mixed for 2 hours at room temperature. Host protein was reduced to 43,058 ppm and aggregates to 3.4%. In one series of experiments conducted at pH 8.0, the sample was fractionated by precipitation with PEG-6000, in separate experiments where the concentration was 600 mM, 800 mM, 900 mM, and 1000 mM (1 M). The precipitates were then washed in PEG, 50 mM Tris, pH 8.0, after which the antibody was resolubilized in 50 mM Tris, pH 8.0. Host protein in that series was reduced to 51, 55, 45, and 41 ppm respectively. Anion exchange particles in the form of Dowex AG1X2 (Bio-Rad) were added to each sample in an amount of 5% v/v and mixed for 60 minutes. Host protein across the series was reduced to 16, 17, 15, and 13 ppm. Another series of experiments was run, identical in all details except the initial PEG precipitation was performed at pH 7.0. Host protein after the PEG step was 44 ppm for the 600 mM NaCl track, 43 ppm for the 800 mM track, 29 ppm for the 900 mM track, and 31 ppm for the 1000 mM track. After Dowex treatment, host protein was reduced to 20, 17, 12, and 16 ppm respectively.

Example 13

An IgG-containing cell culture harvest containing 286,010 ppm host protein contaminants and 23% aggregates was conditioned by addition of 1% allantoin and 0.025% ethacridine, and incubated stirring at room temperature for 1 hour. A 1:1:1:1 mixture of particles (Chelex-100, MacroPrep tButyl, MacroPrep High Q from Bio-Rad), and electropositive metal affinity particles (TREN 40 high from Bio-Works) were mixed, equilibrated to physiological conditions, and settled mixed particles were added to the harvest in a combined amount of 5%, then mixed for 2 hours at room temperature. Host protein was reduced to 38,061 ppm and aggregates to 1.4%. In a series of experiments conducted at pH 8.0, the sample was fractionated by precipitation with PEG-6000, in separate experiments where the concentration of NaCl was 600 mM, 800 mM, 900 mM, and 1000 mM (1 M). The precipitates were then washed in PEG, 50 mM Tris, pH 8.0, after which the antibody was resolubilized in 50 mM Tris, pH 8.0. Host protein was reduced to 79, 69, 56, and 57 ppm respectively. Anion exchange particles in the form of Dowex AG1X2 (Bio-Rad) were added to each sample in an amount of 5% v/v and mixed for 60 minutes. Host protein across the series was reduced to 18, 17, 16, and 13 ppm. Another series of experiments was run, identical in all details except the initial PEG precipitation was performed at pH 7.0. Host protein after the PEG step was 94 ppm for the 600 mM NaCl track, 62 ppm for the 800 mM track, 67 ppm for the 900 mM track, and 46 ppm for the 1000 mM track. After Dowex treatment, host protein was reduced to 28, 9, 23, and 17 ppm respectively.

Example 14

An IgM containing cell culture harvest containing 321,483 ppm host protein and 26% aggregates was conditioned by addition of 1% allantoin, 0.025% ethacridine, and NaCl to produce a conductivity of 25 mS/cm. The mixture was incubated for 1 hour, solids were removed by centrifugation, and the liquid was flowed through a column packed with equal proportions of MacroPrep Tbutyl, Macroprep High Q, Macroprep High S, and Chelex 100, where the volumetric ratio of column to harvest was 5%. Host protein was reduced to 73,663 ppm and aggregates were reduced to 0.8%. The sample was fractionated in parallel but separate experiments, both with 13% PEG-6000 at pH 7, one with 100 mM NaCl, the other with 800 mM NaCl. The precipitates were then washed with 13% PEG, 50 mM Hepes, pH 7.0 to remove the excess salt, then the IgM was resolubilized with 50 mM Hepes, pH 7.0. Host protein at 100 mM NaCl was reduced to 7,411 ppm. Host protein at 800 mM NaCl was reduced to 417 ppm. Aggregate content increased to 1.1%. The samples were applied to an anion exchange monolith (CIM QA, BIA Separations) at pH 7.0 and eluted with a sodium chloride gradient. Host proteins in the sample corresponding to PEG precipitation at 100 mM NaCl were reduced to 1,424 ppm. Host proteins in the sample corresponding to PEG precipitation at 800 mM NaCl were reduced to 63 ppm. Aggregates were less than 0.01% for both preparations.

Example 15

Contaminant removal by caprylic acid precipitation in conjunction with treatment by functionalized particles, followed by PEG precipitation at 800 mM NaCl. Different amounts of caprylic acid were added to cell culture harvest clarified by centrifugation, to final concentrations of 0.1, 0.2, 0.3, 0.4, and 0.5% respectively. Allantoin was added to each sample to a final concentration of 1%. Neither pH nor salt concentration was adjusted. Final pH at 0.4% caprylic acid was 5.4. The mixtures were stirred for 2 hours. Solids were removed by passing the sample through a 0.22 µm microfilter. The filtrate was then passed through a column containing an equal parts mixture of porous particles bearing TREN, iminodiacetic acid, and butyl ligands (WORKBEADS™ TREN 40 High from BioWorks, Chelex-100 from Bio-Rad, and Macro-Prep T-butyl from Bio-Rad, respectively), where the combined volume of particles was 5% of the applied sample volume. Host cell protein was reduced from an original 242,888 ppm of IgG in the harvest to 233,318 in 0.1% caprylic acid; 193,400 ppm in 0.2%; 57,519 ppm at 0.3%; 38,602 ppm at 0.4%; and 42,666 ppm at 0.5%. IgG fragments, including free light chain and light chain dimers were reduced from 12.2% in the harvest to 5.3% at 0.3% caprylic acid; 3.4% in 0.4%; and 3.6% in 0.5% caprylic acid. There was no fragment reduction at 0.1 and 0.2% caprylic acid. Aggregates were reduced from 1.28% in the harvest, to 1.22% in 0.1% caprylic acid, 0.87% in 0.2% caprylic acid, 0.31% in 0.3% caprylic acid, and were undetectable (less than 0.05%) at 0.4 and 0.5% caprylic acid. IgG recovery across the caprylic acid concentrations was 99% in 0.1% caprylic acid, 99% at 0.2%, 95% at 0.3%, 99% at 0.4%, and 95% at 0.5%. After treatment with the mixture of porous particles, host protein was reduced to 4205 ppm in the sample treated with 0.4% caprylic acid, representing a reduction of 98% and leaving the antibody at greater than 99% pure, with 1% fragments and no measurable aggregate, with an overall IgG recovery of 99%. The antibody was further purified by precipitation with polyethylene glycol (PEG-6000), conducted at 20.5% PEG, 800 mM NaCl, 50 mM Hepes, pH 7.0. After PEG precipitation of harvest treated with 0.4% caprylic acid, host proteins were reduced to 11 ppm, aggregates to 0.09%, and light chain fragments were undetectable. After PEG precipitation of harvest treated at 0.5% caprylic acid, host protein was reduced to 13 ppm, aggregates to 0.1%, and light chain fragments were undetectable. These results both correspond to a 99.9995% reduction of host protein. In a parallel control experiment where the harvest was not treated by the present method, PEG precipitation reduced host protein to 67,687 ppm. The more than 6,000-fold improvement provided by the disclosed method illustrates two distinct benefits. The obvious benefit is that reduction of host protein contamination by the present method permits a follow-on method to achieve a yet greater reduction of host protein contamination. It also highlights the benefit that the disclosed methods particularly remove contaminants that interfere with the ability of the purification method itself to achieve its best results.

The present embodiments may be combined with other purification methods to achieve higher levels of purification. Examples of such other purification methods include, but are not limited to, other methods commonly used for purification of IgG, such as protein A and other forms of affinity chromatography, anion exchange chromatography, cation exchange chromatography, hydrophobic interaction chromatography, immobilized metal affinity chromatography, and additional mixed mode chromatography methods; also methods of precipitation, crystallization, and liquid-liquid extraction. It is within the purview of a person of ordinary skill in the art to develop appropriate conditions for the various methods and integrate them with the methods disclosed herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the methods disclosed herein.

Many modifications and variations of the methods disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the disclosed embodiments being indicated by the following claims.

What is claimed is:

1. A method for the purification of an antibody from a protein preparation comprising:
conditioning the protein preparation by contacting the preparation with ethacridine or an electronegative organic additive selected from the group consisting of heptanoic acid, octanoic acid, octenoic acid, nonanoic acid, nonenoic acid, and decanoic acid, thereby removing at least 90% of chromatin, then
(1) precipitating the antibody with polyethylene glycol (PEG) in the presence of non-protein-precipitating salts at a concentration in a range from about 0.2 M to about 2.0 M to provide a precipitate comprising the antibody; or
(2) precipitating the antibody with PEG at a concentration of non-protein-precipitating salts less than 0.15 M to provide a precipitate and subsequently washing the precipitate with the non-ionic organic polymer in the presence of the non-protein-precipitating salts at a concentration in a range from about 0.2 M to about 2.0 M;
wherein the PEG has a polymer size in a range of 1000 to 12,000 Daltons (D), the non-protein-precipitating salts are selected from the group consisting of sodium acetate, potassium acetate, sodium chloride, potassium chloride, and combinations thereof, and the precipitating steps or washing step is optionally carried out in a substantial absence of a protein-precipitating salt.

2. The method of claim 1, wherein the electronegative organic additive is octanoic acid.

3. The method of claim 1, wherein the conditioning comprises contacting the preparation with allantoin at a supersaturating concentration in a range of 0.6 to 50%, 0.7 to 20%, 0.8 to 10%, 0.9 to 5%, or 1 to 2% (w/v).

4. The method of claim 1, wherein the PEG comprises a polymer size in a range of 2000 to 8,000 D, or 3000 to 6000 D, or a polymer size of 1500 D, 3500 D, 4000 D, or 6000 D.

5. The method of claim 1, wherein the non-protein-precipitating salts comprise sodium chloride.

6. The method of claim 1, wherein a net salt concentration of the non-protein precipitating salts in the protein preparation after step (1) is in a range selected from the group consisting of 200 mM to 2 M, 300 mM to 1.5 M, 400 mM to 1 M and 500 mM to 800 mM.

7. The method of claim 1, further comprising washing the precipitate of step (1) with the non-ionic organic polymer in the presence of the non-protein-precipitating salts at a concentration of at least 0.2M, or washing the precipitate with one or more precipitating salts at a concentration sufficient to maintain the antibody in a precipitated state.

8. The method of claim 1, wherein the protein precipitating salt is selected from the group consisting of sodium sulfate, potassium sulfate, ammonium sulfate, sodium phosphate, potassium phosphate, ammonium phosphate, sodium citrate, potassium citrate, ammonium citrate, and combinations thereof.

9. The method of claim 1, wherein the antibody is a naturally occurring protein, a recombinant protein, a monoclonal antibody, an IgG antibody, or an IgM antibody.

10. The method of claim 1, where the protein preparation comprises a bodily fluid, milk, plasma, serum, or a cell culture harvest.

* * * * *